(12) United States Patent
Pasricha et al.

(10) Patent No.: US 9,023,066 B2
(45) Date of Patent: May 5, 2015

(54) MEDICAL TREATMENT DEVICE FOR SUTURING OR LIGATING TISSUE

(75) Inventors: Pankaj Jay Pasricha, Houston, TX (US); Yuji Sakamoto, Hachioji (JP); Satoshi Miyamoto, Hachioji (JP); Yoshio Onuki, Hachioji (JP); Norio Onishi, Fussa (JP)

(73) Assignees: Olympus Corporation, Tokyo (JP); Apollo Endosurgery, Inc., Austin, TX (US)

( * ) Notice: Subject to any disclaimer, the term of this patent is extended or adjusted under 35 U.S.C. 154(b) by 473 days.

(21) Appl. No.: 11/133,002

(22) Filed: May 19, 2005

(65) Prior Publication Data

US 2005/0261708 A1 Nov. 24, 2005

Related U.S. Application Data

(60) Provisional application No. 60/572,987, filed on May 20, 2004.

(51) Int. Cl.
  *A61B 17/04* (2006.01)
  *A61B 17/12* (2006.01)
  *A61B 17/06* (2006.01)

(52) U.S. Cl.
  CPC ....... *A61B 17/12013* (2013.01); *A61B 17/0401* (2013.01); *A61B 17/0467* (2013.01); *A61B 17/0482* (2013.01); *A61B 17/0487* (2013.01); *A61B 17/12009* (2013.01); *A61B 2017/0404* (2013.01); *A61B 2017/0417* (2013.01);

(Continued)

(58) Field of Classification Search
  USPC ............ 606/139, 232, 72, 213, 144, 148, 606/215–217, 228; 289/12–14; 24/115 R, 24/30.5 W
  See application file for complete search history.

(56) References Cited

U.S. PATENT DOCUMENTS

RE34,021 E * 8/1992 Mueller et al. ............... 604/533
5,304,188 A * 4/1994 Marogil ....................... 606/157

(Continued)

FOREIGN PATENT DOCUMENTS

JP  04-058175  2/1992
JP  04-231946  8/1992

(Continued)

OTHER PUBLICATIONS

Official Action dated Dec. 7, 2010 received from the Japanese Patent Office, together with an English-language translation.

*Primary Examiner* — Katherine Dowe
(74) *Attorney, Agent, or Firm* — Scully, Scott, Murphy & Presser, P.C.

(57) ABSTRACT

A treatment device for endoscopic therapy of the present invention includes a suturing-ligating member having a distal end portion and a proximal end portion, that carries out at least one of suturing and ligation of biological tissue, a stopper provided to be movable forward or backward on an proximal end side of the suturing or ligating member, and stoppable by friction on the suturing-ligating member to maintain the biological tissue in a sutured or ligated state by the suturing-ligating member, and a suturing-ligation releasing member provided movable with relative to the suturing-ligating member to release the suturing-ligation state maintained by firctional stopping between the suturing-ligating member and the stopper by moving the releasing member to the proximal end portion side of the suturing-ligating member.

4 Claims, 6 Drawing Sheets

(52) U.S. Cl.
CPC . *A61B2017/0458* (2013.01); *A61B 2017/0464* (2013.01); *A61B 2017/0475* (2013.01); *A61B 2017/0488* (2013.01); *A61B 2017/0496* (2013.01); *A61B 2017/06052* (2013.01)

(56) References Cited

U.S. PATENT DOCUMENTS

| | | | | |
|---|---|---|---|---|
| 5,312,436 | A | * | 5/1994 | Coffey et al. ................. 606/228 |
| 5,517,729 | A | * | 5/1996 | Shaffer ...................... 24/30.5 R |
| 5,570,690 | A | * | 11/1996 | Yoon ............................ 600/587 |
| 5,855,586 | A | * | 1/1999 | Habara et al. ................ 606/144 |
| 2002/0133917 | A1 | * | 9/2002 | Chu ................................ 24/429 |
| 2003/0144673 | A1 | | 7/2003 | Onuki et al. |
| 2003/0236535 | A1 | | 12/2003 | Onuki et al. |
| 2004/0050395 | A1 | * | 3/2004 | Ueda et al. .................... 128/899 |
| 2004/0092964 | A1 | * | 5/2004 | Modesitt et al. .............. 606/144 |
| 2005/0085691 | A1 | * | 4/2005 | Nakao ........................... 600/128 |

FOREIGN PATENT DOCUMENTS

| | | |
|---|---|---|
| JP | 06-017712 | 1/1994 |
| JP | 10-000194 | 1/1998 |
| JP | 10-500318 | 1/1998 |
| JP | 10-081358 | 3/1998 |
| JP | 11-103911 | 4/1999 |
| JP | 2001-158469 | 6/2001 |
| JP | 2002-253562 | 9/2002 |
| JP | 2004-000601 | 1/2004 |

* cited by examiner

MEDICAL TREATMENT DEVICE FOR SUTURING OR LIGATING TISSUE

CROSS-REFERENCE TO RELATED APPLICATIONS

This application claims the benefit of U.S. Provisional Application No. 60/572,987, filed May 20, 2004.

BACKGROUND OF THE INVENTION

1. Field of the Invention

The present invention relates to a treatment device for biological tissue for endoscopic treatment, and more particularly, to a treatment device for suturing or ligating an internal biological tissue in combination with an endoscope.

2. Description of the Related Art

A device that sutures or ligates an internal tissue under endoscopic observation is disclosed in U.S. Pat. Appln. Publication No. 2003/0236535A1. The device disclosed in this U.S. patent application publication can suture or ligate the tissue by penetrating a ligature having a fixing member through the tissue.

In case where a desired region cannot be sutured or ligated by means of a device such as the one represented in this U.S. patent application publication, the ligature must be cut to cancel a sutured or ligated state. The ligature can be thus cut by endoscopically using, for example, a scissor forceps or the like. If the ligature is buried in the tissue, however, forceps operation for cutting the ligature without injuring the tissue is very troublesome.

On the other hand, the fixing member for fixing a suture or ligature to the biological tissue may be removed by being endoscopically grasped with a grasping forceps or the like. If the fixing member has a shape such that it cannot be grasped easily, in this case, however, the forceps operation is very troublesome.

BRIEF SUMMARY OF THE INVENTION

An object of the present invention is to provide a device and a method for easily releasing suturing or ligation carried out in biological tissue by means of an endoscopic treatment.

According to an aspect of the present invention, there is provided a treatment device for biological tissue, capable of suturing or ligating a biological tissue under endoscopic observation and of releasing the tissue from a sutured or ligated state by simple operation.

According to another aspect of the present invention, there is provided a treatment device for endoscopic therapy, comprising:

a. suturing-ligating member having a distal end portion and a proximal end portion, that carries out at least one of suturing and ligation of biological tissue;

a stopper provided to be movable forward or backward on an proximal end side of the suturing or ligating member, and stoppable by friction on the suturing or ligating member to maintain the biological tissue in a sutured or ligated state by the suturing or ligating member; and a suturing-ligation releasing member provided movable with relative to the suturing or ligating member to release the suturing or ligation state maintained by firctional stopping between the suturing or ligating member and the fixing member by moving the releasing member to the proximal end portion side of the suturing or ligating member.

Advantages of the invention will be set forth in the description which follows, and in part will be obvious from the description, or may be learned by practice of the invention. Advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

DETAILED DESCRIPTION OF THE INVENTION

[First Embodiment]

FIGS. 1 to 5 show a medical treatment device according to a preferred first embodiment of the present invention.

(Configuration)

Figure 1:
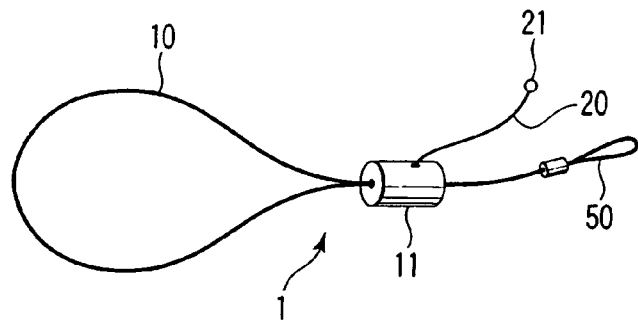
FIG. 1 is a schematic general view of a treatment device according to a first embodiment of the present invention.

As shown in FIG. 1, the medical treatment device according to the present embodiment is formed as a device for ligating biological tissue. The treatment device 1 can be used to ligate, e.g., a polyp before respecting it, thereby restraining bleeding effectively. The treatment device 1 comprises a loop-shaped ligature 10, a silicone tube 11 through which the ligature 10 is passed, and a flexible wire 20 connected to the silicone tube 11 and having an enlarged portion 21 on its distal end.

The ligature 10 is provided with a loop-shaped or ring-shaped operating section 50 on its proximal end portion. Although the flexible wire 20 shown in FIG. 1 is only one in number, two or more flexible wires may be used in place of it. Since too many flexible wires may possibly exert adverse effects, such as entangling the treatment device 1 indwelt in a human body, one or two flexible wires 20 should preferably be used. Further, the flexible wire 20 may be formed having a belt-shaped structure in place of the elongate linear structure as illustrated.

(Function)

FIGS. 2 to 5 illustrate functions of the treatment device 1 described above.

Figure 2:
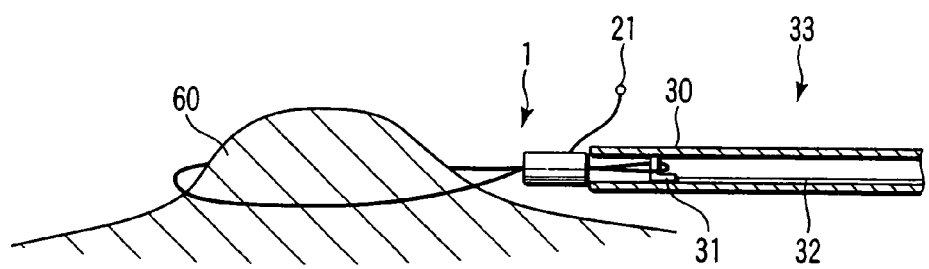
FIG. 2 is a schematic view showing a state in which a biological tissue is ligated with use of the treatment device of FIG. 1.

As shown in FIG. 2, the treatment device 1 is used in combination with a ligator 33, which is composed of a ligation sheath 30, a hook wire 32, and an operating handle (not shown) for operating the hook wire 32. The hook wire 32 has on its distal end a hook 31 that engages the operating section 50 of the ligature 10.

Figure 3:
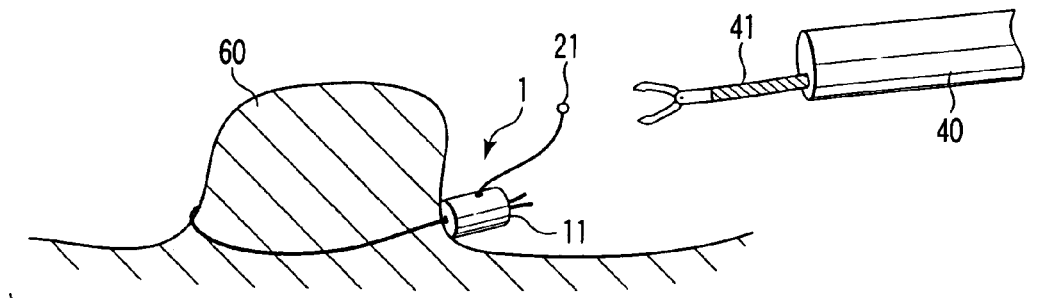
FIG. 3 is a schematic view showing a state in which the ligation of the biological tissue is completed.

In ligation, the loop-shaped ligature 10 is hitched to a target tissue 60, and the hook 31 is pulled to contract the loop of the ligature 10. Thereafter, the silicone tube 11, which serves as a stopper is pushed toward the target tissue 60 with the distal end portion of the ligation sheath 30, and moved along the ligature 10 in the direction further to contract the loop of the ligature 10, whereby the target tissue 60 is ligated with the silicone tube 11 being stopped by friction on the ligature 10. FIG. 3 shows a state in which the target tissue 60 is ligated and proximal-end-side odds of the ligature 10 that project from the silicone tube 11 are cut.

Figure 4:
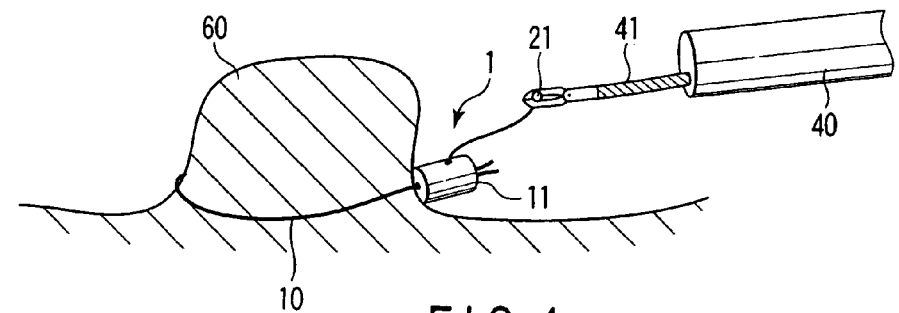
FIG. 4 is a schematic view showing the way the biological tissue is released from the ligated state.
Figure 5:
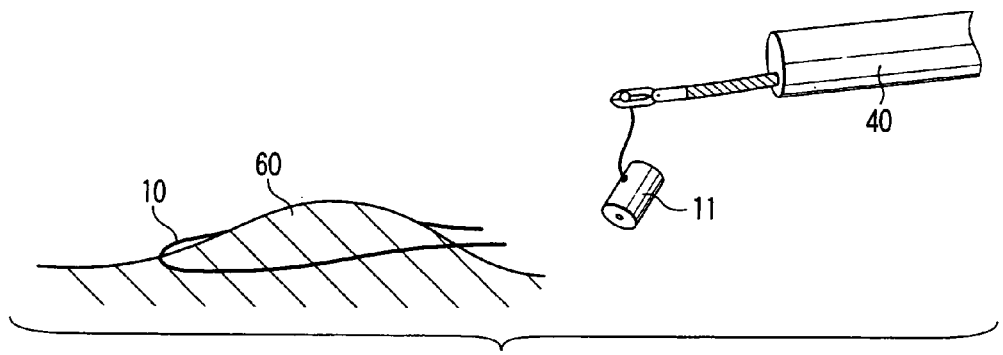
FIG. 5 is a schematic view showing completion of the release of the biological tissue from the ligated state.

Preferably, a scope 40 having a channel through which a grasping forceps 41 can be passed, as shown in FIGS. 3 and 4, should be used in canceling the ligated state. The flexible wire 20 is grasped by the grasping forceps 41 that is inserted into the human body through the scope 40, and pulled with a force greater than the frictional fixing force of the silicone tube 11. Thereupon, the silicone tube 11 is moved to the proximal end side of the ligature 10 and disengaged from the ligature 10. FIG. 5 shows a state in which the ligation is canceled.

The flexible wire 20 can be grasped more easily through an endoscope than when the silicone tube 11 is grasped directly. Thus, the silicone tube 11 can be easily moved to the proximal end side from any direction without adversely influencing the tissue during manipulation. The enlarged portion 21 on the distal end of the flexible wire 20 can prevent the grasping forceps 41 from failing to grasp the tissue. The flexible wire 20, which serves as a suturing-ligature releasing member, may be formed of any material that is flexible and strong enough to stand a pull when ligation is canceled. Preferably, it should be made of a stretched polyamide-based synthetic fiber, a material for a conventional suture, such as polypropylene, polyethylene terephthalate, or polytetrafluoroethylene, or a bioabsorbable material, such as polyglycol acid, for example. Further, the flexible wire 20 may be either a monofilament or a twisted yarn. In view of visibility, moreover, white, red, and yellow that resemble the colors of biological tissues are not preferred as the color of the flexible wire 20. Furthermore, the color of the wire should be different from that of the ligature 10.

[Second Embodiment]

FIGS. 6 to 11 show a treatment device 2 according to a second embodiment of the present invention. The following various embodiments or modifications are basically the same as the foregoing embodiment, so that like numerals refer to like regions of the foregoing embodiment, and a detailed description of those regions is omitted.

(Configuration)

Figure 6:
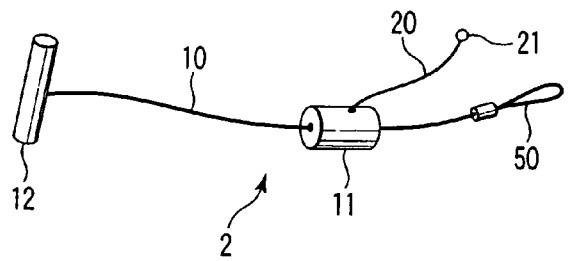
FIG. 6 is a schematic general view of a treatment device according to a second embodiment.

The second embodiment differs from the first embodiment in that the treatment device 2 according to the present embodiment is provided with a cylindrical member 12 on its distal end portion without the formation of a loop-shaped form in a ligature 10, as shown in FIG. 6.

(Function)

FIGS. 7 to 10 illustrate functions of the treatment device 2 according to the second embodiment.

Figure 7:
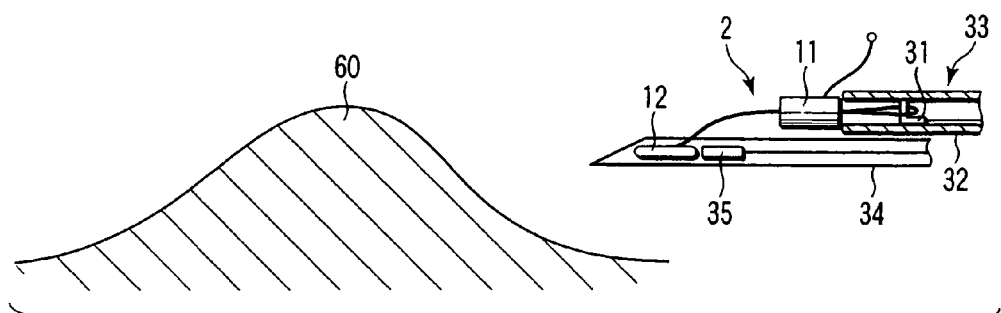
FIG. 7 is a schematic view showing a state in which a biological tissue is ligated with use of the treatment device according to the second embodiment.

As shown in FIG. 7, the treatment device 2 is used in combination with a ligator 33, which resembles the one according to the first embodiment, and a hollow puncture needle 34, which has a push wire 35 inside and can store the cylindrical member 12.

Figure 8:
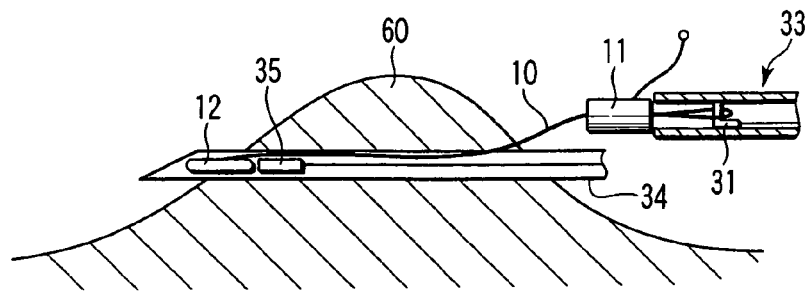
FIG. 8 is an explanatory view showing a state in which a puncture needle is passed through the biological tissue.
Figure 9:
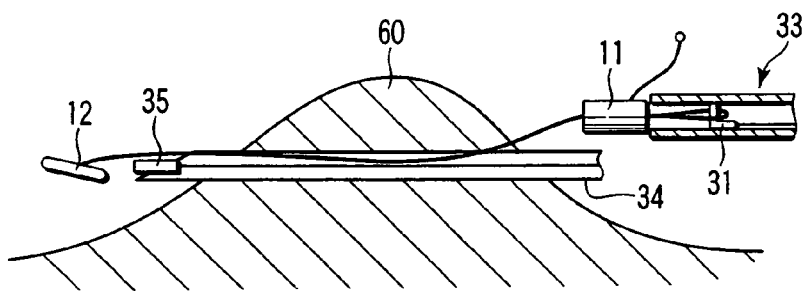
FIG. 9 is an explanatory view showing a state in which a cylindrical member attached to a ligature is pushed out of the distal end of the puncture needle.
Figure 10:
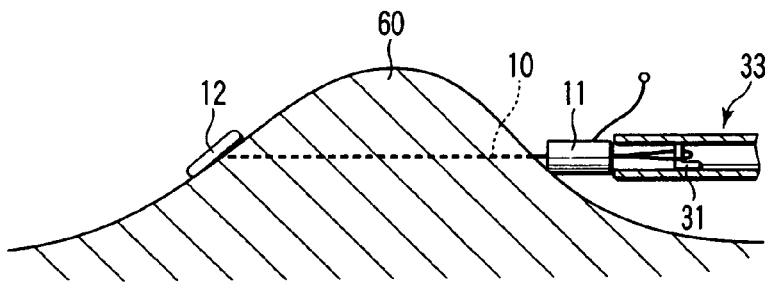
FIG. 10 is an explanatory view showing a state after the puncture needle is drawn out of the biological tissue.

First, the puncture needle 34 through which the cylindrical member 12 is passed is inserted through the target tissue 60, as shown in FIG. 8. Thereafter, the push wire 35 is advanced toward the distal end of the puncture needle 34, whereby the cylindrical member 12 is discharged out of the puncture needle 34, as shown in FIG. 9. Thereafter, the puncture needle 33 is drawn out of the tissue 60, as shown in FIG. 10, whereupon the target tissue 60 can be ligated in the same manner as in the first embodiment by pulling the hook 31.

Figure 11:
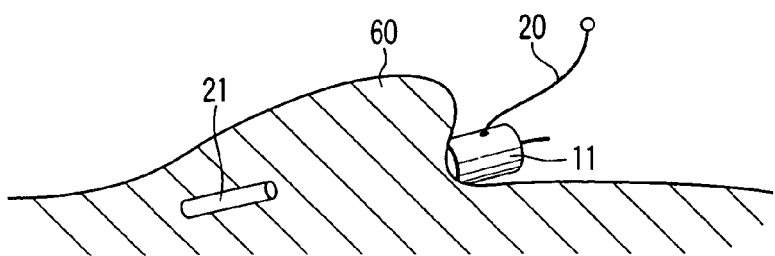
FIG. 11 is an explanatory view showing a state after completion of ligation of the biological tissue.

FIG. 11 shows a state the target tissue 60 is ligated by means of the treatment device 2. In releasing the target tissue 60 from the ligation, a flexible wire 20 is pulled with a grasping forceps or the like, as in the first embodiment. Thus, a silicone tube 11 is moved to the proximal end side of the ligature 10 and disengaged from it, whereupon the ligated state can be canceled.

Besides the effects of the first embodiment, according to the present embodiment, the cylindrical member 12 that fixes the target tissue 60, along with the ligature 10, penetrates the target tissue 60, so that the ligature 10 can be prevented from coming off the tissue during the ligation.

[First Modification]

Figure 12:
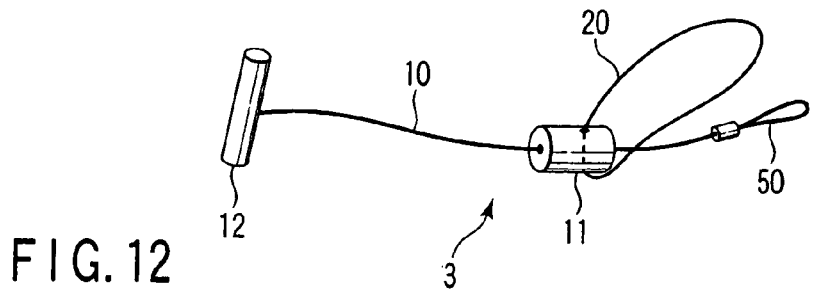
FIG. 12 is a schematic general view of a treatment device according to a first modification.

FIG. 12 shows a modification of the second embodiment.

(Configuration)

The modification differs from the second embodiment in that a treatment device 3 according to the present embodiment has a loop-shaped flexible wire 20, which is passed through a hole that is bored in a silicone tube 11 in the direction perpendicular to its lumen axis, as shown in FIG. 12.

(Function)

According to this treatment device 3, which also enjoys the same functions and effects of the second embodiment, the flexible wire 20 is loop-shaped so that it can be easily grasped to ensure pulling force greater than in the case of a single wire.

[Third Embodiment]

Figure 13:
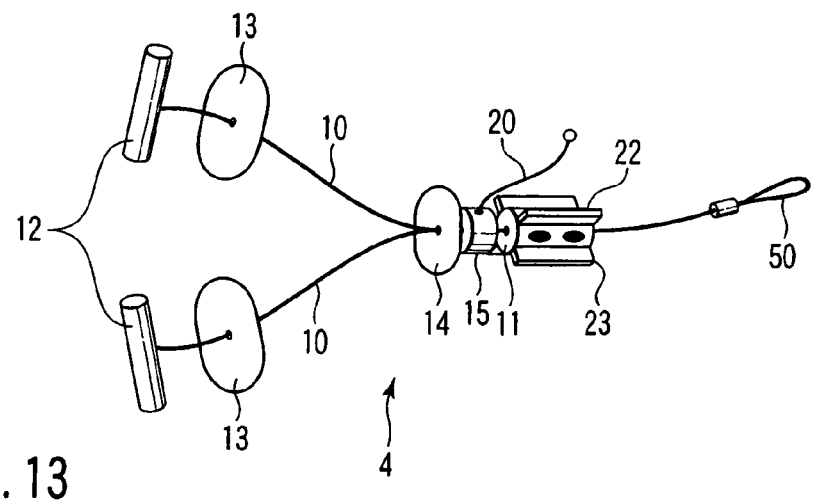
FIG. 13 is a schematic general view of a treatment device according to a third embodiment.
Figure 14:
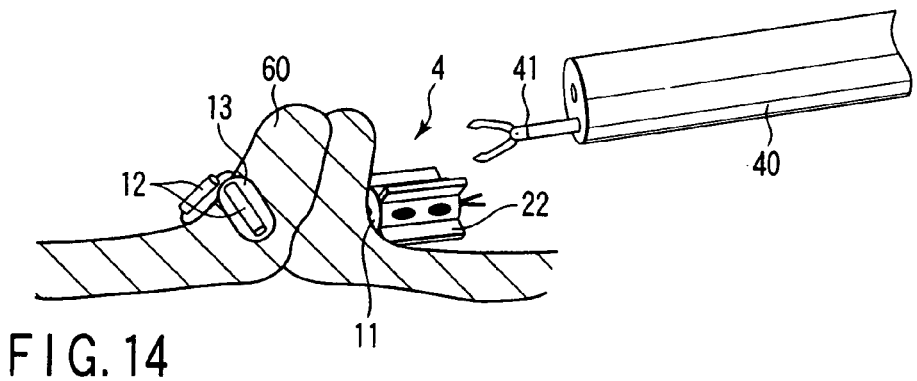
FIG. 14 is a schematic view showing a state after a biological tissue is sutured with use of the treatment device according to the third embodiment.
Figure 15:
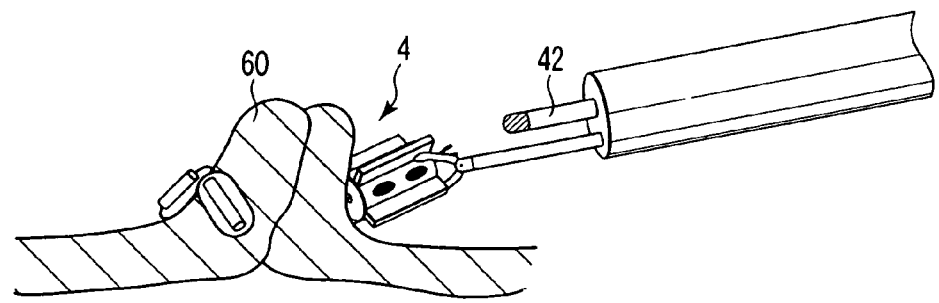
FIG. 15 is an explanatory view showing the way the sutured state is canceled.

FIGS. 13 to 15 show a third embodiment of the present invention.

(Configuration.)

The third embodiment differs from the second embodiment in that a treatment device 4 according to the present embodiment is formed to be used to suture the target tissue 60, as shown in FIG. 13. For example, it can be practically used to suture and close perforations such as ulcers in the target tissue 60, for example.

This treatment device 4 is designed so that two ligatures 10 having a cylindrical member 12 each are passed through a silicone tube 11. The respective proximal end portions of the two ligatures 10 are connected to each other, and a ring- or loop-shaped operating section 50 is provided on the proximal end. Each ligature 10 is provided with a distal-side pledget 13, which is located in a position between each cylindrical member 12 and the silicone tube 11 and near the cylindrical member 12 and has a central hole through which the ligature 10 is passed. Further, a hand-side pledget 14 is located in a position between the cylindrical members 12 and the silicone tube 11 and near the silicone tube 11. It has a central hole through which the ligature 10 is passed.

The silicone tube 11 is provided integrally with four outwardly projecting blade-shaped grip members 22 in place of a flexible wire 20. Further, the silicone tube 11 is provided integrally with a magnet 23.

The two ligatures 10 are passed through a tearing-preventive tube 15 in a position near the silicone tube 11. The tearing-preventive tube 15 is provided with the flexible wire 20 that has an enlarged portion 21.

(Function)

The same functions and effects of the second embodiment can be obtained according to this treatment device 4. Since the treatment device 4 is provided with the distal-side pledgets 13 and the hand-side pledget 14, moreover, the cylindrical members 12 and the silicone tube 11 can be prevented from being buried in the target tissue 60 even after the suturing.

If the silicone tube 11 is situated in a position such that it cannot be easily seized with a grasping forceps, as shown in FIG. 14, the silicone tube 11 can be moved to a position for easy grasping by magnetically attracting the magnet 23, which is attached to the silicone tube 11, with use of a magnet forceps 42 that is passed through the channel of the scope 40, as shown in FIG. 15. Since the silicone tube 11 is provided with the grip members 22, moreover, slipping of the grasping forceps 41 can be prevented when the silicone tube 11 is seized with the grasping forceps 41. Thus, the silicone tube 11 can be securely grasped with a greater force as it is moved and disengaged.

Since the grip members 22 are provided integrally on the silicone tube 11, they can be prevented from coming off the silicone tube 11 when they are trailed. Further, the tearing-preventive tube 15 can restrain the two ligatures 10 from being spread to expand the bore of the silicone tube 11 by the repulsive force of the target tissue 60 during the suturing process, thereby preventing the silicone tube 11 from being damaged. By grasping the flexible wire 20 attached to the tearing-preventive tube 15 with the grasping forceps 41 or the like and pulling it, the tearing-preventive tube 15 can be trailed to move and disengage the silicone tube 11 so that the sutured state is canceled.

The pledgets 13 and the hand-side pledget 14 may be formed of any material that is flexible and strong enough to stand the repulsive force of the tissue and pressures from the ligatures 10 and the cylindrical members. Preferably, they should be made of PTFE or silicone resin, for example. Further, they can enjoy higher visibility if their colors are different from those colors, such as red, yellow, etc., which resemble the colors of organic tissues.

[Second Modification]

Figure 16:
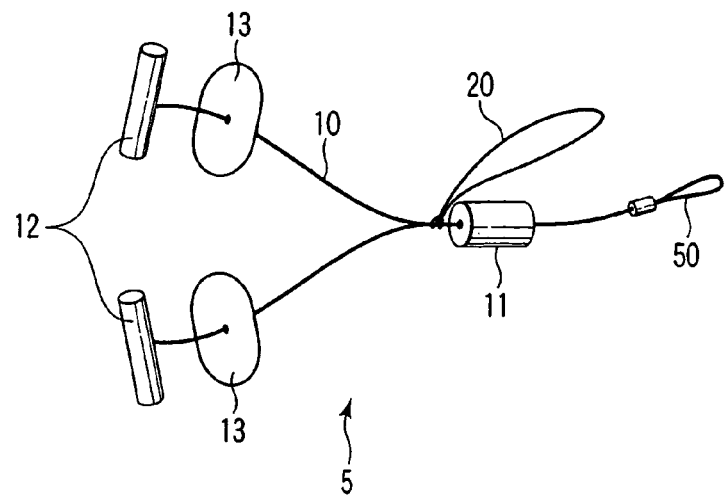
FIG. 16 is a schematic general view of a treatment device according to a second modification.
Figure 17:
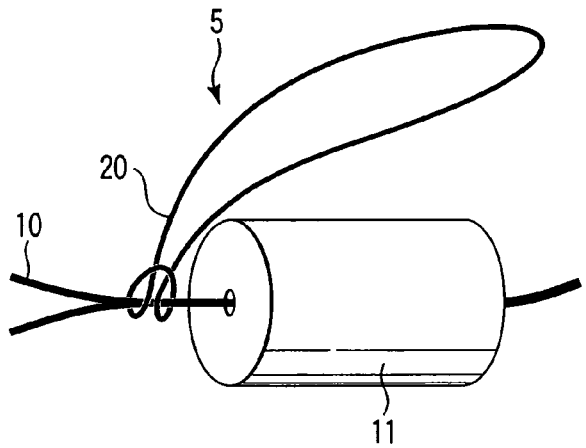
FIG. 17 is an enlarged view of a part of FIG. 16.

A second modification shown in FIGS. 16 and 17 is a modification of the third embodiment.

(Configuration)

As shown in FIG. 16, a treatment device 5 according to the second modification differs from the third embodiment in the following particulars.

First, a silicone tube 11 is provided with neither grip members 22 nor a magnet 23. Secondly, a loop-shaped flexible wire 20, in place of the tearing-preventive tube, is slidably wound around a ligature, as shown in FIG. 17. In this modification, as shown in FIG. 17, the flexible wire 20 is wound in a manner such that one ring portion is passed through the other ring portion.

(Function)

According to this treatment device 5, which enjoys the same functions and effects of the third embodiment, further functions and effects can be obtained such that the number of components used therein can be reduced to ensure high productivity, and that the loop-shaped flexible wire 20 can be easily grasped to ensure pulling force greater than in the case of a single wire.

[Fourth Embodiment]

Figure 18:
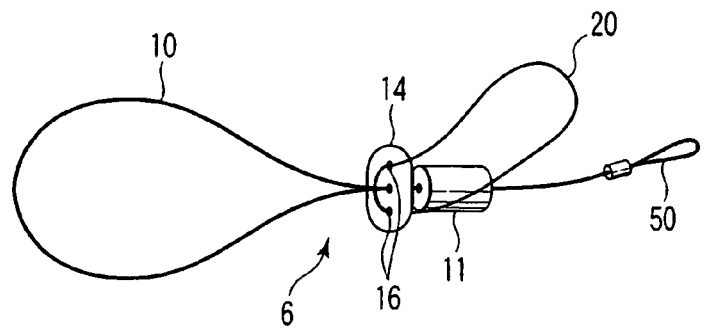
FIG. 18 is a schematic general view of a treatment device according to a fourth embodiment.

FIG. 18 shows a fourth embodiment of the present invention.

(Configuration)

A treatment device 6 according to the fourth embodiment differs from the first embodiment in the following particulars.

As shown in FIG. 18, the treatment device 6 according to the present embodiment is provided with a hand-side pledget 14 having a central hole through which a ligature 10 is passed. The pledget 14 is situated near the distal end side of a silicone tube 11 on the ligature 10. A loop-shaped flexible wire 20 is passed through two holes 16 that are arranged symmetrically with respect to the hole of the hand-side pledget 14 through which the ligature 10 is passed. The flexible wire 20 is slidably passed through the two holes 16 in the hand-side pledget.

(Function)

This treatment device 6 can provide the following functions and effects, besides the same functions and effects of the first embodiment.

Since the flexible wire 20 is attached to the hand-side pledget 14, the flexible wire 20 can be prevented from being buried in the tissue. The loop-shaped flexible wire 20 is slidable with respect to the hand-side pledget 14. If any part on the flexible wire 20 is grasped as it is pulled, therefore, the flexible wire 20 slides on the hand-side pledget 14 so that it extends in a straight line from its junction with the hand-side pledget 14 to a grip position. Thus, the silicone tube 11 can be easily trailed without dispersion of the pull force.

[Third Modification]

Figure 19:
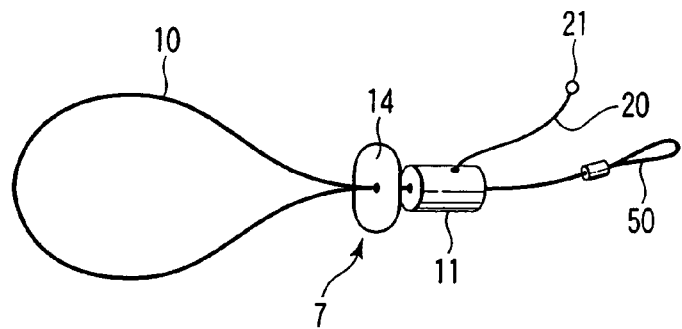
FIG. 19 is a schematic general view of a treatment device according to a third modification.

A third modification shown in FIG. 19 is a modification of the fourth embodiment.

(Configuration)

In a treatment device 7 according to the present modification, as shown in FIG. 19, unlike the fourth embodiment, a flexible wire 20 having an enlarged portion 21 on its distal end is connected to a hand-side pledget 14.

(Function)

According to this treatment device 7, compared with the fourth embodiment, the flexible wire 20 is shaped so that it is not space-consuming when the treatment device 7 is indwelt in the human body. Thus, food or the like or the scope 40 or grasping forceps 41 can be prevented from catching the flexible wire 20 during release operation.

[Fifth Embodiment]

Figure 20:
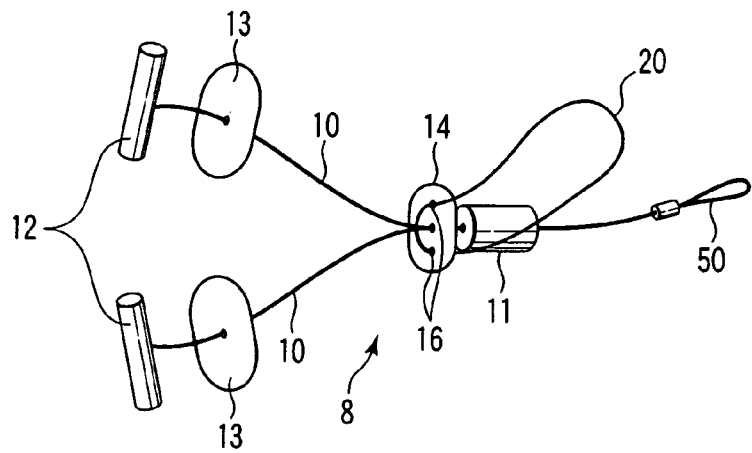
FIG. 20 is a schematic general view of a treatment device according to a fifth embodiment.
Figure 21:
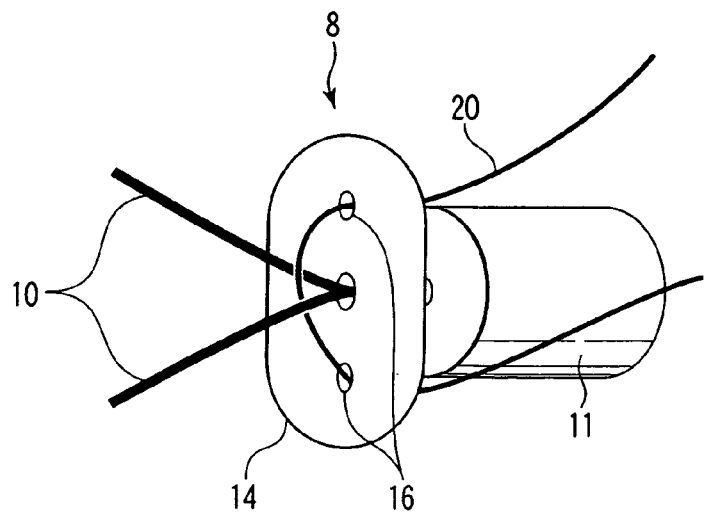
FIG. 21 is an enlarged view of a part of FIG. 20.

FIGS. 20 and 21 show a fifth embodiment of the present invention.

(Configuration)

A treatment device 8 according to the fifth embodiment differs from the treatment device 7 according to the fourth embodiment in the following particulars.

Two ligatures 10 having a cylindrical member 12 each are passed through a silicone tube 11. A distal-side pledget 13 is located in a position between the cylindrical member 12 on each ligature 10 and the silicone tube 11 and near the cylindrical member 12. The ligature 10 is passed through a hole in its central portion. As shown in FIG. 21, a loop-shaped flexible wire 20 that is attached to a hand-side pledget 14 passes between the two ligatures 10 as it passes from one of two holes 16 in the hand-side pledget 14 to the other.

(Function)

According to this treatment device 8, which also enjoys the same functions and effects of the fourth embodiment, the distal-side pledgets 13 prevent the cylindrical members 12 from being buried in the target tissue 60. Since the loop-shaped flexible wire 20 passes between the two ligatures 10, the lumen axis of the silicone tube 11 is always coaxial with the direction in which the flexible wire 20 is pulsed. Thus, resistance between the silicone tube 11 and the ligatures 10 is minimized, so that the silicone tube 11 can be trailed with a smaller force.

Additional advantages and modifications will readily occur to those skilled in the art. Therefore, the invention in its broader aspects is not limited to the specific details and representative embodiments shown and described herein. Accordingly, various modifications may be made without departing from the spirit of the general inventive concept.

What is claimed is:

1. A treatment device for endoscopic therapy, comprising:
    a suturing-ligating member having a distal end portion and a proximal end portion, that is configured to carry out at least one of suturing and ligation of biological tissue;
    a stopper having a distal end portion and a proximal end portion and positioned on the suturing-ligating member such that the suturing-ligating member projects from both the proximal and distal end portions of the stopper, wherein the stopper is movable forward or backward along the suturing-ligating member and stoppable by friction on the suturing-ligating member, such that the stopper is configured to keep the biological tissue in a sutured or ligated state by the suturing-ligating member;
    wherein the suturing-ligating member has a cut end formed as a result of cutting an odd portion of a proximal end portion side of the suturing-ligating member projecting from the proximal end portion of the stopper kept by friction, so that the treatment device is configured to be indwelt in a body in a state where the distal end portion of the suturing-ligating member ligates or sutures the biological tissue together with the stopper; and
    a suturing-ligation releasing member comprising a flexible wire looped around the suturing-ligating member at a position distal of the distal end portion of the stopper and not connected to the stopper, such that the releasing member is slidably attached to the suturing-ligating member and is configured to be moved independently of the suturing-ligating member,
    wherein, when the suturing-ligation releasing member is pulled toward the proximal end portion of the suturing-ligating member, the suturing-ligation releasing member presses against the stopper and the stopper is pressed toward the proximal end portion of the suturing-ligating member from the distal end portion thereof to be moved to the proximal end portion of the suturing-ligating member, thereby, releasing a suturing-ligation state maintained by friction between the suturing-ligating member and the stopper,
    and wherein the suturing-ligating member has the suturing-ligation state and a suturing-ligation releasing state, wherein in the suturing-ligation state, the biological tissue is ligated or sutured by fixing the stopper by friction on the suturing-ligating member, and in the suturing-ligation releasing state, the biological tissue is released from ligation or suture by separating the suturing-ligation releasing member and the stopper from the suturing-ligating member by pulling the suturing-ligation releasing member with a force larger than the friction toward a proximal end portion of the suturing-ligating member.

2. The treatment device according to claim 1, further comprising a fixing member provided on the distal end portion of the suturing-ligating member to fix the suturing-ligating member to the biological tissue.

3. The treatment device according to claim 2, further comprising:
    a hollow puncture needle containing a push wire to be movable forward and backward thereinside and configured to pierce through the biological tissue while the fixing member is disposed within the hollow puncture needle; and
    a ligating instrument including a wire configured to hook the distal end portion of the suturing-ligating member and a sheath through which the wire is movably inserted, and configured to carry out at least one of the suturing and ligation by advancing the sheath while the wire is hooking the distal end portion of the suturing-ligating member to move the stopper forward and fastening the biological tissue with the suturing-ligating member.

4. The treatment device according to claim 1, further comprising:
    a ligating instrument including a wire configured to hook the distal end portion of the suturing or ligating member and a sheath through which the wire is movably inserted, and configured to carry out at least one of the suturing and ligation by advancing the sheath while the wire is hooking the distal end portion of the suturing-ligating member to move the stopper forward and fastening the biological tissue with the suturing-ligating member.

* * * * *